United States Patent [19]

Petrus

[11] Patent Number: 5,965,137

[45] Date of Patent: Oct. 12, 1999

[54] INSECT REPELLENT COMPOSITION AND METHOD FOR INHIBITING THE TRANSMISSION AND TREATMENT OF SYMPTOMS OF VECTOR-BORNE DISEASES

[75] Inventor: Edward J. Petrus, Austin, Tex.

[73] Assignee: Advanced Medical Instruments, Austin, Tex.

[21] Appl. No.: 09/192,421

[22] Filed: Nov. 16, 1998

[51] Int. Cl.$^6$ .......................... A61K 33/30; A61K 35/78
[52] U.S. Cl. .................. 424/195.1; 424/641; 424/642; 514/725
[58] Field of Search .............................. 424/195.1, 641, 424/642; 514/725

[56] References Cited

U.S. PATENT DOCUMENTS

| | | | |
|---|---|---|---|
| 4,923,894 | 5/1990 | Kanda et al. | 514/493 |
| 4,963,591 | 10/1990 | Fourman et al. | 514/944 |
| 4,970,220 | 11/1990 | Chaussee | 514/358 |
| 5,198,218 | 3/1993 | Kuznitz et al. | 424/401 |
| 5,747,058 | 5/1998 | Tipton et al. | 424/423 |

OTHER PUBLICATIONS

Fisher GJ, Vorhees JJ, Retinoic Acid Prevents Vitamin A Deficiency Caused By UV Light In Skin. Nature Medicine 1999;5:376–377, 418–422.

Marinho, H.A. et al., European J. of Clinical Nutrition, vol. 45(11), p. 539–544, Nov. 1991.

Brud, W.S. et al., Proceedings: vol. 2, Keynote Presentations, p. 13–23, 1990.

Singh, D. et al., Insect. Sci. Applic., vol. 12(4), p. 487–491, Aug. 1991.

Bekele, A.J. et al., Int. J. of Pest Management, vol. 4292), p. 139–142, 1996.

Ntiamoah, Y.A. et al., Entomologia Experimentalis et Applicata, vol. 79(2), p. 219–226, May 1996.

Roth, G.N. et al., J. Nat. Prod., vol. 61(4), p. 542–545, 1998.

Jembere, B. et al., Bulletin of Entomological Research, vol. 85(3), p. 361–367, 1995.

Russell, G.B. et al., Phytochemistry, vol. 35(6), p. 1455–1456, 1994.

Don–Pedro, K.N., Pestic. Sci., vol. 46(1), p. 79–84, Jan. 1996.

Ge, X. et al., J. Econ. Entomol., vol. 88(6), p. 1771–1775, Dec. 1995.

*Primary Examiner*—Jean C. Witz

[57] ABSTRACT

A topical composition for the delivery of bio-affecting agents through the protective outer layer of skin into the underlying tissues and into the general circulation to prevent the causes and symptoms of vector-borne diseases. The transdermal penetration is achieved by the use of an essential volatile oil with insect repellent capabilities, such as eucalyptus oil. The bio-affective agents may be a combination of a zinc salt and form of vitamin A. A zinc salt may also be used for photoprotective purposes. The topical composition can be formulated as a solution, suspension, cream, ointment, gel, film or spray.

15 Claims, No Drawings

INSECT REPELLENT COMPOSITION AND METHOD FOR INHIBITING THE TRANSMISSION AND TREATMENT OF SYMPTOMS OF VECTOR-BORNE DISEASES

FIELD OF THE INVENTION

The present invention relates to a novel composition of an insect repellent with bio-active agents delivered transdermally by a penetration enhancer to prevent and treat vector-borne diseases.

BACKGROUND OF THE INVENTION

Forty percent of the world's population lives in regions where malaria is endemic. According to WHO, malaria affects 500 million people annually and kills from 1.5 to 2.7 million people, about twice as many as from AIDS. Some 600,000 children die of malaria alone each year, and over one million die of malaria in conjunction with other illnesses, a rate of one child every 30 seconds. The worldwide incidence of the disease has quadrupled in the past five years, and resistance to available drugs for prevention and treatment is growing rapidly.

It is believed that malaria was introduced into the United States by European colonists (P. vivax and P. marariae) and African slaves (P. falciparum) in the 16th and 17th centuries. Malaria was among the most common reasons for hospitalization during the Civil War, with the two sides reporting more than 1.2 million cases between them. Hippocrates was the first to associate malaria incidence with the proximity to stagnant water. British physician Ronald Ross proved that malaria is carried not by air or water but by mosquitoes, a discovery for which he was awarded a Nobel Prize.

Malaria is caused by infection by protozoan parasites of the genus Plasmodium. More than a hundred species of this parasite exist, capable of infecting reptiles, birds, rodents and primates. Four species of Plasmodium that cause human malaria, P. vivax, P. falciparum, P. ovale, and P. malariae, are transmitted by the bite of infective female mosquitoes of the genus Anopheles. Anophelene species capable of transmitting malaria are found in all 48 states of the contiguous United States. Global warming may expand the habitat of the anopheles mosquito, and WHO has warned that an extra 80 million cases of malaria annually may be reported by the end of the next century.

Humans are the intermediate host and reservoir of the parasite, and the mosquito is the definitive host and vector. In vector-borne diseases, the mosquito serves as a vector, and the virus or parasite, must breed in the mosquito. Breeding amplifies the level of parasites or viruses in the mosquito's salivary glands and makes it possible for the insect to pass the parasite or virus to the next host by dribbling the virus or parasite into the skin or bloodstream with its saliva. Transmission occurs primarily between dusk and dawn. In malaria, when an infected mosquito takes a blood meal, it injects sporozites from its salivary glands into the bloodstream of the host. The sporozoites infect hepatocytes in the liver and begin a process of development and multiplication, which causes severe fevers with hot and cold chills. The life cycle is completed when an anopheline takes a blood meal and ingests male and female gametocytes, allowing for sexual reproduction. It takes approximately 8 to 13 days for the completion of this cycle for P. vivax and P. falciparum. Malaria parasites have a voracious appetite and in just a few hours can suck as much as a quarter pound of hemoglobin from red blood cells in an infected man. The parasites destroy red blood cells and clog blood vessels damaging the brain and causing heart failure, respiratory distress, kidney failure, bleeding disorders and causing injury to other vital organs.

Vector-borne diseases have become a global health problem. The Aedes aegypti mosquito, originally from Africa, is known to spread yellow fever, dengue and dengue hemorrhagic fever. The Aedes albopictus mosquito, from Asia, is known to spread several types of equine encephalitis virus, dengue, dengue hemorrhagic fever, and recently, canine heartworm. Keeping the mosquito from biting people is the best approach today and the goal of the current invention.

Vaccines have been difficult to develop since the parasite moves between organs, changing its appearance from stage to stage, and hiding inside red blood cells from the immune system. The difficulty in designing a vaccine was outlined in Business Week, Sep. 21, 1998, pp. 70–72. Quinine, from the bark of the cinchona tree in South America, and extracts of the wormwood plant in China were among the first effective antimicrobial agents used. Chloroquine, a synthetic antimalarial drug eradicates parasites, but resistance is now widespread. Many other drugs are available, but most have undesirable side effects. Rosenthal P J, *Emerging Infectious Diseases* 4(1):49–57, 1998.

A recent study by the Johns Hopkins School of Public Health and the Papua New Guinea Institute of Medical Research investigated the ability of vitamin A and zinc to boost the immunity to malaria. The study, as reported by UNICEF, was conducted on nearly 800 children in Papua New Guinea, and reported a decrease in the number and severity of malaria cases. The 13 month study as reported in *The Economist,* Aug. 1, 1998, noted a 30% reduction in the incidence of malaria with vitamin A, and 40% fewer attacks with 10 mg of zinc. It was felt that the zinc strengthened the immune system's "killer" T cells and raised the level of antibodies to Plasmodium.

Insect repellents to prevent the mosquito from biting the human or animal is the most logical approach to suppressing these vector-borne diseases. Insect repellents that are topically applied to deter mosquitoes from biting consist of chemical compositions or essential oils. The chemical compositions may be chosen from a group consisting of: N,N-diethyl toluamide (DEET), N,N-diethyl benzamide, dimethyl phytate, ethyl hexanediol, indalone, di-n-propylisocinchoronate, bicycloheptene dicarboxide, tetrahydro furaldehyde, among others. DEET, the most popular, is toxic and known to cause skin irritation, irritability, and seizures. Indalone and ethyl hexanediol are known to cause liver and kidney damage.

Insect repellents may be chosen from a group consisting of essential oils and active ingredients of essential oils. Essential oils are defined as any class of volatile oils obtained from plants possessing the odor and other characteristic properties of the plant. Examples of repellent compounds that are essential oils includes: almond bitter oil, anise oil, basil oil, bay oil, caraway oil, cardamon oil, cedar oil, celery oil, chamomile oil, cinnamon oil, citronella oil, clove oil, coriander oil, cumin oil, dill oil, eucalyptus oil, fennel oil, ginger oil, grapefruit oil, lemon oil, lime oil, mint oil, parsley oil, peppermint oil, pepper oil, rose oil, spearmint oil (menthol), sweet orange oil, thyme oil, turmeric oil, and oil of wintergreen. Examples of active ingredients in essential oils are: citronella, methyl salicylate, ethyl salicylate, propyl salicylate, citronellol, safrole, and linonene.

The preferred essential oil of this invention is eucalyptus oil. Oil of eucalyptus is obtained by aqueous distillation of the fresh leaves of the eucalyptus tree. There are about 300 species, but most of the oil is extracted from *Eucalyptus globulus*. The oils may be divided into three classes of commercial importance: (1) the medicinal oils, which contain substantial amounts of eucalyptol, also known as cineol; (2) the industrial oils, containing terpenes, which are used for flotation purposes in mining operations; and (3) the aromatic oils, such as *E. citriodora*, which is characterized by their aroma. Eucalyptus oil, the volatile oil from *E. globulus*, contains: 70–80% cineole (eucalyptol), a-pinene, phellandrene, terpineol, citronellal, geranyl acetatges, eudesmol, eudesmyl acetate, and piperitone. The oil of *E. citriodora*, emits a delightful lemon scent and contains up to 98 per cent of citronellol. Medicinal eucalyptus oil is probably the most powerful antiseptic of its class. It has a disinfectant action, forms ozone on exposure to air, and its antiseptic properties confer some antimalarial action. For some years, eucalyptus-chloroform was employed as one of the remedies in the tropics for hookworm. In veterinary practice, eucalyptus oil is administered to horses in influenza, to dogs in distemper, to all animals in septicemia, and for parasitic skin afflictions.

Many commercial insect repellents use eucalyptus oil, cedar oil or various essential oil blends. Price, in U.S. Pat. No. 4,587,123, discloses the use of eucalyptus oil in shampoos to reduce pest infestations in animals. He reported that tests revealed that the repellent effectively eradicated and repelled fleas and mosquitos for up to four consecutive days. It was also noted that the composition aided in healing irritated skin from insect bites. The effectiveness of the composition in humans was short lived and had to be topically applied every one to two hours.

Eucalyptus oil also has skin penetrating characteristics. Zupan, U.S. Pat. No. 4,560,553 disclosed the use of eucalyptus oil as a skin permeation enhancing agent coupled with an anti-microbial. Penetration enhancing substances allow the infiltration of medications and chemical agents through the skin, and may be enzymatic or non-enzymatic. Penetration enhancers include but are not limited to alcohols, such as ethanol and isopropanol; polyols, such as n-alkanols, limonene, terpenes, dioxolane, propylene glycol, ethylene glycol, other glycols, and glycerol; sulfoxides, such as dimethylsulfoxide (DMSO), dimethylformamide, methyl dodecyl sulfoxide, dimethylacetamide; esters, such as isopropyl myristate/palmitate, ethyl acetate, butyl acetate, methyl proprionate, and capric/caprylic triglycerides; ketones; amides, such as acetamides; oleates, such as triolein; various surfactants, such as sodium lauryl sulfate; various alkanoic acids, such as caprylic acid; lactam compounds, such as azone; alkanols, such as oleyl alcohol; and admixtures thereof.

To prolong the duration of the effectiveness of eucalyptus oil, both as an insect repellent and a penetration enhancing agent, it is the object of the present invention to add a zinc salt to the eucalyptus oil composition. Allen in U.S. Pat. No. 4,895,727 discloses the addition of a zinc salt to an active agent to reduce the transdermal flux through the skin and mucus membrane of the pharmaceutically active agent creating a reservoir effect in the skin and mucous membrane.

Clinical manifestations of malaria begins when free merozoites invade erythrocytes. Zinc is primarily bound to albumin and transported to the liver where some is stored and the rest delivered to extrahapatic tissues. In the plasma, zinc is localized in erythrocytes and leucocytes. Experiments show that zinc-deficient rats have osmotic fragility of erythrocytes. Kraus A, Rogh H P, Kirchgessner M. *Arch Tierernahr* 1997;50(3):257–69. Administering zinc was shown to decrease irreversible sickling in patients with sickle cell anemia by affecting the erythrocyte cell membrane. Prasad A S. *Annals of Internal Medicine,* 15 Jul. 1996. 125:142–44. Zinc is an essential mineral found in every form of life on earth. Unlike other metals, zinc is virtually nontoxic. Zinc and its compounds have long been recognized as possessing certain therapeutic functions. Zinc compounds are acknowledged as astringents and beneficial in wound healing, reducing inflammation, and has antimicrobial, antifungal and antiviral activity. Zinc is the active agent in formulations to treat diaper rash, decubitus ulcers, and abrasions. Zinc stabilizes the cell membranes and inhibits the formation of free radicals. Zinc also strengthens the integrity of blood vessel walls by reducing the membrane permeability and stopping bleeding. Zinc has an inhibitory effect on the release of histamine from mast cells due to its stabilizing effect of the mast cell membrane. Zinc also has chelating capabilities, and is an excellent chelator of iron and lead. The parasite, P. falciparum, is an iron dependent pathogenic organism. The effect of zinc on the incidence of malaria may also be related to cellular mediated immunity.

In a preferred form of the invention, the composition uses a zinc salt such as zinc acetate. Zinc salts are selected from a group consisting of, but not limited to: zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate.

Zinc status influences several aspects of vitamin A metabolism, including its absorption, transport, and utilization. Christian P, West K P Jr. *Am J Clin Nutr* 1998 Aug;68(2 Suppl):435–441 S. Studies have shown a causal relationship between vitamin A, and retinol, a form of vitamin A, and malaria. Retinol levels were inversely correlated with malaria parasitemia. Sturchler D., et al. *Acta Trop* 1987 Jun;44(2):213–27. One of the causes of malaria, P. falciparum, is retinol-sensitive and favorably responds to retinol therapy to clinically treat the symptoms of malaria. Davis T M, Skinner-Adams T S, Beilby J. *Acta Trop* 1998 May;69(2):111–9. Vitamin A deficiency was shown to increase the severity of malarial infection in rats. Stoltzfus R J, Harvey P W, Nesheim M C. *J Nurtr* 1989 Dec;119(12):2030–7. There is also a low plasma retinol level in malaria patients. Thurnham D I, Singkamani R. *Trans R Soc Trop Med Hyg* 1991 Mar–Apr;85(2):194–9.

Zinc salts may also provide photoprotection against ultraviolet (UV) damage to the skin. Zinc oxide provides protection against both UVA and UVB radiation. Mitchnick et al, in U.S. Pat. No. 5,733,531 discloses a sunblock formulation using zinc oxide particles. Tapley in U.S. Pat. No. 5,573,753 discloses a sunscreen of zinc oxide in oil. Mitchell et al, in U.S. Pat. No. 5,587,148 discloses a sunblock of micronized particles of zinc oxide. However, Hausler in U.S. Pat. No. 4,349,536 discloses the use of zinc and copper salts to promote a suntan by stimulating melanin production.

None of the foregoing patents mention or suggest the application of bio-affective agents, such as zinc salts and vitamin A delivered to the skin and bloodstream by means of an insect repellent such as eucalyptus oil with penetrating capabilities.

SUMMARY OF THE INVENTION

It is the object of this invention to provide a novel composition that prevents insects from infecting humans or animals by use of a topical application of an essential oil with insect repellent qualities, such eucalyptus oil, combined with a soluble zinc salt that prolongs the effectiveness of the repellent.

It is a further embodiment of the invention to deliver a form of vitamin A and zinc to the bloodstream by means of a penetration enhancer.

It is another embodiment of the invention to provide photoprotection by the addition of zinc salts to the composition.

DETAILED DESCRIPTION OF THE INVENTION

The present invention relates to novel compositions for topical application and delivery of bio-affecting agents through the protective outer layer of the skin, into the underlying tissues and into the general circulation. The term "bio-affecting agent" refers to any chemical substance or formulation which beneficially affects the body. The bio-affective agents of the preferred composition comprises, zinc salts and a form of vitamin A, added to a penetration enhancer, such as eucalyptus oil, an essential volatile oil, with insect repellent qualities, to form a solution, suspension, cream, ointment, gel, film, or spray.

The concentration of the bio-affecting agents in the composition can also vary greatly and will be dependent upon may factors, e.g. type, bioavailability, potency, surface area to which it is applied, composition used and the amount of the penetrating agents used. The concentration of bio-affecting agents will vary from about 0.1 % to 25 % of the total composition, and may be suspended or dissolved.

A wide variety of therapeutic agents is known which can provide beneficial effects when absorbed into the systemic circulation. Formulation of such systemically effective therapeutic agents in combination with a penetration enhancer facilitates penetration through the skin and the amount absorbed into the systemic circulation. This topical administration offers a significant advantage over oral administration of therapeutic agents by overcoming the difficulty of poor gastrointestinal absorption, by using a lower dosage than required orally, and is rapidly metabolized by the liver (first pass effect). Antimalaria agents may also be mixed with the composition.

Eucalyptus oil, the volatile oil from E. globulus, contains: 70–80% cineole (eucalyptol), and varying amounts of: a-pinene, phellandrene, terpineol, citronellal, geranyl acetatges, eudesmol, eudesmyl acetate, and piperitone. The oil of E. citriodora contains up to 98 per cent of citronellol. Eucalyptus oil is used as both an insect repellent and penetration enhancer and in the preferred composition represents about 5% to about 20% by weight relative to the total composition.

Eucalyptus oil mixes readily with an equal amount of alcohol which can be selected from a group consisting of ethanol, isopropyl and normal propyl alcohols, methanol, and butyl alcohols. The preferred composition contains about 10% to 30% ethanol by weight relative to the total composition.

The bio-affective agents of the preferred composition includes, zinc salts and a form of vitamin A. Zinc salts are in two forms, as a zinc ion, and as a microfine zinc salt dispersion. The term "zinc ion" means that the zinc-atom portion of the zinc salt is dissociated into simple or complex zinc ions dispersed in a liquid medium. Zinc salts are selected from a group consisting of, but not limited to: zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate. The preferred composition contains about 0.1 % to 10 % zinc salt by weight for ionization relative to the total composition.

Vitamin A is a fat-soluble vitamin that consists of a group of substances that include retinol, retinal and the carotenoids. Beta-carotene is the precursor form of vitamin A derived from plants. Vitamin A has the ability to scavenge free radicals and reduce the risk of developing some types of cancer. Normal serum levels of retinol are 300–700 ng/ml in adults and 200–500 ng/ml in infants. Retinol is conjugated, then oxidized to produce retinoic acid and retinal. The preferred composition contains about 0.1% to 5 % of vitamin A by weight of the total composition.

Photoprotection is provided by the transdermal absorption of zinc ions, but may be augmented by the addition of suspended microfine zinc salt particles, such as zinc oxide, comprising 0.2 to 20% by weight of the total composition. Zinc ions function by inhibiting the inflammatory reaction to the skin by stabilization of the lysosomal membranes and inhibition of prostaglandin synthesis. Suspended zinc oxide particles are highly reflective of UV light.

A surfactant may be selected from the group consisting of, but not limited to: sodium lauryl sulfate, magnesium lauryl sulfate, sodium lauroyl sarcosinate, polyethylene glycol stearate, polyethylene glycol monostearate, coconut monoglyceride sulfonates, sodium alkyl sulfate, sodium alkyl sulfoacetates, copolymers of polyethylene and polybutylene, allypolyglycol, copolymers of polyoxybutylene and polysxylethylene. The preferred surfactants are sodium or magnesium lauryl sulfate.

This novel composition can be formulated as a solution, suspension, cream, ointmemt, gel, film or spray. The composition may also include various additional agents and ingredients such as fragrances, preservatives, antioxidants, gelling agents, thickening agents, stabilizers, surfactants, emolients, coloring agents, aloe vera, waxes, other penetration enhancers, and the like.

Many variations of the present invention will suggest themselves to those skilled in the art in light of the above-detailed description. For example, any essential volatile oil or combination of volatile oils may be employed. Further, many bio-affective agents or combination of agents may be employed. All such obvious modifications are within the full intended scope of the appended claims.

Prior art does not teach or suggest the combination of elements described in the specifications or as defined in the claims. The advantages of delivering the bio-affective agents by absorbtion by both the skin and the bloodstream by means of an essential oil with insect repellent capabilities are readily apparent.

What is claimed is:

1. A topical composition for inhibiting the transmission of vector-borne diseases and for the treatment of symptoms of vector-borne diseases in mammals consisting essentially of (a) an effective amount of an essential volatile oil with insect repellent and transdermal penetration capabilities;

(b) an effective amount of a zinc salt;

(c) an effective amount of vitamin A; and (d) one or more ingredients selected from the group consisting of antimalarial medications, fragrances, preservatives, antioxidants, gelling agents, thickening agents, stabilizers, surfactants, emollients, coloring agents, aloe vera, waxes and penetration enhancers.

2. The topical composition of claim 1, wherein said essential volatile oil is selected from the group consisting of: almond bitter oil, anise oil, basil oil, bay oil, caraway oil, cardamon oil, cedar oil celery oil, chamomile oil, cinnamon oil, citronella oil, clove oil, coriander oil, cumin oil, dill oil, eucalyptus oil, fennel oil, ginger oil, grapefruit oil, lemon oil, line oil, mint oil, parsley oil, peppermint oil, pepper oil, rose oil, spearmint oil, menthol, sweet orange oil, thyme oil, turmeric oil, and oil of wintergreen.

3. The topical composition of claim 1, wherein the zinc salt is selected from the group consisting of zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate zinc stannate, zinc tannate, zinc titanate, zinc tetrafluoroborate, zinc gluconate, and zinc glycinate.

4. The topical composition of claim 1, wherein the vitamin A is selected from the group consisting of: retinoic acid, retinol, retinol, carotenoids, and beta-carotene.

5. The topical composition of claim 2, wherein said essential volatile oil represents 5 to 20 % by weight relative to the total composition.

6. The topical composition of claim 3, wherein the zinc salt represents 0.1 to 10 % by weight relative to the total composition.

7. The topical composition of claim 4, wherein the vitamin A represents 0.1 to 5 % by weight relative to the total composition.

8. The topical composition of claim 2, wherein the essential volatile oil is eucalyptus oil.

9. The topical composition of claim 3, wherein the zinc salt is zinc sulfate.

10. The topical composition of claim 4, wherein the vitamin A is retinol.

11. The topical composition as defined by claim 1, wherein the zinc salt also acts as a photoprotective agent.

12. The topical composition of claim 11, wherein the zinc salt is zinc oxide as a suspension of microfine particles.

13. The topical composition of claim 12, wherein the zinc oxide represents 0.2 to 20% by weight of the total composition.

14. The topical composition of claim 1, wherein said composition is formulated as a solution, suspension, cream, ointment, gel, film or spray.

15. A method for inhibiting the transmission of vector-borne diseases and for the treatment of symptoms of vector-borne diseases comprising administering to a mammal in need thereof:
    a) an effective amount of an essential volatile oil with insect repellent and transdermal penetration capabilities, and
    b) an effective amount of one or more bioaffective agents selected from a group consisting of zinc salts and vitamin A.

\* \* \* \* \*